US012220200B2

United States Patent
Mitra et al.

(10) Patent No.: US 12,220,200 B2
(45) Date of Patent: Feb. 11, 2025

(54) DEVICE, SYSTEM AND METHOD FOR REAL TIME MONITORING AND ANALYSIS OF HEALTH PARAMETERS RELATING TO NON-COMMUNICABLE DISEASES

(71) Applicants: ALL INDIA INSTITUTE OF MEDICAL SCIENCES, NEW DELHI, New Delhi (IN); BIOART AZURE RESEARCH & DEVELOPMENT PRIVATE LIMITED, West Bengal (IN)

(72) Inventors: Dipendra Kumar Mitra, New Delhi (IN); Kallol Mallick, Kolkata (IN); Randeep Guleria, New Delhi (IN); Aparajit Ballav Dey, New Delhi (IN); Rajiv Narang, New Delhi (IN); Anant Mohan, New Delhi (IN); Rakesh Kumar Deepak, New Delhi (IN)

(73) Assignees: ALL INDIA INSTITUTE OF MEDICAL SCIENCES, NEW DELHI, New Delhi (IN); BIOART AZURE RESEARCH & DEVELOPMENT PRIVATE LIMITED, West Bengal (IN)

( * ) Notice: Subject to any disclaimer, the term of this patent is extended or adjusted under 35 U.S.C. 154(b) by 260 days.

(21) Appl. No.: 17/783,798

(22) PCT Filed: Dec. 9, 2020

(86) PCT No.: PCT/IN2020/051012
§ 371 (c)(1),
(2) Date: Jun. 9, 2022

(87) PCT Pub. No.: WO2021/117059
PCT Pub. Date: Jun. 17, 2021

(65) Prior Publication Data
US 2023/0000352 A1   Jan. 5, 2023

(30) Foreign Application Priority Data

Dec. 9, 2019  (IN) .............................. 201911050866

(51) Int. Cl.
A61B 5/00        (2006.01)
A61B 5/318       (2021.01)
A61B 5/1172      (2016.01)

(52) U.S. Cl.
CPC ............ A61B 5/002 (2013.01); A61B 5/0077 (2013.01); A61B 5/318 (2021.01); A61B 5/1172 (2013.01)

(58) Field of Classification Search
CPC ...................................... A61B 5/00
See application file for complete search history.

(56) References Cited

U.S. PATENT DOCUMENTS

| 2008/0255432 A1* | 10/2008 | Nielsen | A61B 5/7475 600/301 |
| 2012/0265029 A1* | 10/2012 | Fahey | A61B 5/14552 600/301 |
| 2015/0164438 A1* | 6/2015 | Halperin | G16H 20/10 340/573.1 |

OTHER PUBLICATIONS

Moeen Hassanalieragh et al., "Health Monitoring and Management Using Internet-of-Things (IoT) Sensing with Cloud-based Processing: Oppurtunities and Challenges", 2015 IEEE International Conference on Services Computing, New York, NY, Jun. 27, 2015-Jul. 2, 2015, pp. 285-292. DOI: 10.1109/SCC.2015.47.

(Continued)

Primary Examiner — Khoi V Le
(74) Attorney, Agent, or Firm — Wenderoth, Lind & Ponack, L.L.P.

(57) ABSTRACT

Present invention provide a system and a method for recording, evaluating, screening and monitoring life style associated Non-communicable diseases related data of a subject via an Integrated Medical Device (IMD) in real time, and (Continued)

sharing the same on a server, either local or cloud based, for fast, active sharing of data by remote users anytime anywhere.

19 Claims, 6 Drawing Sheets

(56) References Cited

OTHER PUBLICATIONS

International Search Report and Written Opinion, dated Mar. 26, 2021, issuing in PCT/IN2020/051012.
International Preliminary Report on Patentability, dated May 17, 2022, issuing in PCT/IN2020/051012.

* cited by examiner

DEVICE, SYSTEM AND METHOD FOR REAL TIME MONITORING AND ANALYSIS OF HEALTH PARAMETERS RELATING TO NON-COMMUNICABLE DISEASES

FIELD OF INVENTION

The present invention generally relates to device, system and method for real time monitoring and analysis of pre-defined set of health parameters/data and if desire, transmitting or retrieving the parameters/data wholly or selectively to remote place(s). The present invention particularly relates to real time screening, monitoring and analysis of health-related parameters relating to life-style related non-communicable diseases including, cardio-pulmonary, geriatric and metabolic diseases. The present invention relates not only to real time screening, monitoring and analyzing heath related parameters/data of a subject but also transmitting the parameters/data to any required place(s).

BACKGROUND OF INVENTION

Real time monitoring and recording a subject's (e.g. a patient namely human or animal) medical parameters in a health institute, such as a hospital is the most important step for screening and providing health checkups and diagnosing lifestyle associated non-communicable diseases as stated above at early stages to prevent or control the further disease progression. Electronic monitoring and recording devices which are connected to the subject by suitable electrical wires have been in use since a long time now. However, the data collected from such devices for monitoring and recording are sometimes restricted to the physical location of the health institute at which tests and other analysis are performed.

At times there are needs for immediately sending the data/parameters to another facility or to super specialty facility in case of emergency or for specialized interpretation as well as opinion. Also, there is a need to share data from a number of facilities for facilitating the doctors or other health professionals to access the data anytime when it is needed without waiting for emails, or other type of data transfer methods.

Therefore, there is a need for a device, system and method that may overcome the above-mentioned short comings.

SUMMARY OF INVENTION

It is an objective of the present invention to provide a health care system that is able to monitor, collect, analyze and record data pertaining to health parameters, related and not limited to non-communicable disease related data in real time, where such data can be shared on a cloud based server facilitating other remote users to access the data anytime from anywhere.

Another objective of the present invention to provide a health care method which is capable of monitoring, collecting, analyzing and/or recording related data/parameters pertaining to health of a subject, not limited to non-communicable disease, in real time, where such data/parameters can be shared on a cloud based server facilitating other remote users to access the data anytime from anywhere.

Yet another object of the present invention relates to a seating or lying device for monitoring and sharing health-related data of an individual under test (IUT) in real time.

The foregoing and other objects, features and advantages of the invention will be apparent from the following more particular descriptions of exemplary embodiments of the invention.

An aspect of the present invention provides a system for monitoring and sharing health-related data in real time, comprising: a data capturing device installed with one or more sensors for sensing bio-signals associated with health-related parameters of an individual under test (IUT) and recording the sensed health-related data, where the data capturing device includes a communication interface for communication; a local server communicating locally with the data capturing device for receiving, storing and sharing the recorded health-related data, where the sharing is based on appropriate authentication mechanism to access the local server; a central remote server communicating with the data capturing device and the local server, individually or in combination, for receiving, storing and sharing the recorded health-related data, where the sharing is based on appropriate authentication mechanism to access the central remote server; a first user device communicating locally with the data capturing device via the communication interface over a local communication channel, where the first user device receives the recorded health-related data from the data capturing device over the local communication channel and informs a first user with the recorded health-related data; and a second user device communicating remotely with the data capturing device via the communication interface or communicating remotely with the first user device over a remote communication channel and the remote server, individually or in combination, for receiving and informing a second user with the recorded health-related data from the data capturing device or the first user device, individually or in combination, and wherein configuration of the local server (and any other server in the system) includes only a parent server address associated at least with the central remote server; and wherein server components of the local server and the central remote server (and any other server in the system) in each level of hierarchy of the system are all identical instances of the central remote server; and wherein the IUT is identified uniquely across the system by a multi-system unique identifier mechanism that identifies and authenticates the IUT to use and access the data capturing device or the local server or the central remote server, individually or in combination, thereby providing the system with flexibility and on-demand hierarchy alteration.

An embodiment of the system provides the multi-system unique identifier mechanism (MSUID) is a unique identification which is uniquely associated with the IUT along with all tests and diagnosis related to the IUT, thus the IUT is identified with their unique identifier all over the hierarchy of the system including the local and the central servers, and thus, identified remotely to all devices and facilities communicating with the local and the central servers; and wherein the multi-system unique identifier mechanism for creating unique identification for the IUT is implemented at a lowest level of the hierarchy of the system including the data capturing device; and wherein the MSUID at least includes at least in part a Government/authorized authority issued identification document bearing an identifier associated with the IUT.

Another embodiment of the system provides the MSUID further includes a unique identifier associated with the data capturing device along with the IUT's unique identifier, and wherein all data including the tests and the results and interactions pertaining to the IUT is mapped to his/her unique MSUID, and is synchronized between components in the hierarchy of the system to ensure matching of the MSUID with the unique identification of each IUT to all the data.

An embodiment of the system provides the one or more sensors are either directly integrated with the data capturing device or are communicating with the data capturing device via wired or wireless communication, individually or in combination.

An embodiment of the system provides the one or more sensors communicate with the data capturing device via wired communication or wireless communication, individually or in combination, wherein the wired communication including at least in part electric wires or cables, and wherein the wireless communication includes short-range communication including Bluetooth or infrared individually or in combination.

An embodiment of the system provides the local communication channel includes LAN communication channel or Bluetooth or infrared, individually or in any combination; and wherein the remote communication channel includes wireless LAN, WAN, Internet, Ethernet, WiFi, WLAN, cellular communication channel, individually or in any combination.

Another embodiment of the system provides the recorded health-related data is collected for a particular IUT and is transferred to a scalable server including the local and over cloud to the central remote servers, via the first user device or the second user device or the data capturing device, individually or in any combination, for informing the first and the second users, including at least local attendants, operators, nurses, doctors, specialty doctor, to search, view, evaluate, interpret, write comments/suggestions and print health-related reports.

Yet another embodiment of the system provides the data capturing device further include one or more processing units, memory storage, supporting circuitry and power supply, and wherein the communication interface is a wired or wireless interface, individually or in combination; and the data capturing device further includes an input unit and an output unit, and wherein the one or more sensors are operated using the input and output units; and wherein the input unit includes touch screen panel, non-touch screen panel, buttons or push keys, microphone, individually or in any combination; and wherein the output unit includes a display, speaker, LEDs, LCDs, glow lights individually or in any combination, and wherein the output unit serves a double purpose of displaying of the tests results, and interaction with the IUT.

An embodiment of the system provides the first user device and the second user device include a computer, a laptop, a smart phone, a mobile phone, a mobile device individually or in any combination; and wherein the health-related data recorded is monitored in real time on the first user device and the second user device using an output unit, including at least a display; and wherein the first user device and the second user device print the health-related data at a printer.

Another embodiment of the system provides the system further includes one or more district servers communicating with the local server which in turn communicates with the central remote server, in the hierarchy of the system, and wherein the any other server in the system includes at least the district servers, and wherein the configuration of the district server includes only a parent server address associated at least with the central remote server; and wherein server components of the local server, the district servers and the central remote server in each level of hierarchy of the system are all identical instances of the central remote server, thereby providing the system with flexibility and on-demand hierarchy alteration; where in the one or more district servers are removable from the hierarchy of the system, by simply changing the parent server ID of all individual local servers, which are reporting to the specific district server, to the central remote server's network ID.

An embodiment of the system provides the authentication mechanism to access the local and the central remote servers include one or more of a user name, a password, identification information, an ID number, a PIN, an IP address, a security key, a biometric, a fingerprint, or voice, individually or in any combination.

An aspect of the present invention also provides a method for monitoring and sharing health-related data in real time, comprising: sensing, by a data capturing device installed with one or more sensors for bio-signals associated with health-related parameters of an individual under test (IUT); recording, by the data capturing device, the sensed health-related data, where the data capturing device includes a communication interface for communication; receiving, by a first user device communicating locally with the data capturing device via the communication interface over a local communication channel, the recorded health-related data from the data capturing device over the local communication channel and informing a first user with the recorded health-related data via the first user device; receiving, storing and sharing, by a local server locally communicating with the data capturing device, the recorded health-related data from the data capturing device or the first user device, individually or in combination, where the sharing is based on appropriate authentication mechanism to access the local server; and receiving, storing and sharing, by a central remote server communicating with the data capturing device or the local server or the first user device, individually or in any combination, the recorded health-related data from the data capturing device or the local server or the first user device, individually or in any combination, where the sharing is based on appropriate authentication mechanism to access the central remote server; and receiving, by a second user device communicating with the central remote server, the recorded health-related data from the data capturing device or the first user device or the local server, individually or in combination, and informing a second user with the recorded health-related data via the second user device, and wherein configuration of the local server (and any other server in the method) includes only a parent server address associated at least with the central remote server; and wherein server components of the local server and the central remote server (and any other server in the method) in each level of hierarchy are all identical instances of the central remote server; and wherein the IUT is identified uniquely across the hierarchy by a multi-system unique identifier mechanism that identifies and authenticates the IUT to use and access the data capturing device or the local server or the central remote server, individually or in combination, thereby providing the method with flexibility and on-demand hierarchy alteration.

Another aspect of the present invention also provides a seating device for monitoring and sharing health-related data of an individual under test (IUT) in real time, comprising a body including one or more operating electronic/electrical/mechanical/software components, either individually or in any combination, for controlling operation of the seating device; a set of arm rests attached to the body to provide arm rests to the individual under test (IUT), the set of arm rests including and supporting a camera to capture image/video feed of the individual under test (IUT), a communication interface for operably connecting the seating device with external devices, an Oxygen saturation finger probe, a set of ECG probes for right and left arms of the individual under test (IUT) and an adjustable stand to hold a display unit for display; an ECG plate holder, attached at the bottom of the body, including a spring connected insulated surface to hold a set of ECG plates for right leg and left leg; a set of retractable cabinets, attached to left and right side of the body, to hold a plurality of medical instruments; and a weighing machine communicating with the operating electronic/electrical/mechanical/software components of the body, either individually or in any combination, and where the weighing machine is operably attached to the body.

An embodiment of the present invention provides the operating electronic/electrical/mechanical/software components of the body of the seating device include one or more of processors, memory, drivers, installed with software components or applications for running software algorithms, power switches, power circuits, communication interfaces, or display units, either individually or in any combination.

An embodiment of the present invention provides the seating device includes a Linux Mother Board and Windows Mother Board along with their SMPS and HDD drive for individuals, power circuits, USB Extenders for communication of individual Bio Sensor interfaces.

Another embodiment of the present invention provides the camera in the seating device is situated in front side to capture image/video feed of the individual under test (IUT), and the camera is an image camera, or a video camera, or a web cam, either individually or in any combination, communicating with external devices, and wherein the communication interface includes at least one of a jack, an output Audio Jack for interfacing with audio/video devices, USB inputs and an Ethernet Input Socket, either individually or in any combination.

Yet another embodiment of the present invention provides the display unit in the seating device is a display or a monitor for display, and wherein the display unit includes a monitor, an LED, or an LCD, and the display unit is either a touch screen display or a non-touch screen display for operations. In an embodiment of the present invention, the display unit is attached with input unit including a keyboard, to input data.

Yet another embodiment of the present invention relates to the seating device which device is a fixed device or mobile device, and the mobility can be imparted by providing wheels/rollers and it can be operated manually or by machine. Further, the device can be chair, a bed, a sofa, a recliner, a treadmill, a cycle, stretcher, and the like and these device can be made of any suitable materials such as metal, wood, plastic, and the like. Furthermore, the leg rest, backrest and armrest of the seating device can be selectively folded in order to change the shape of the structures into horizontal/supine positions so that the subject can lying down and all health parameters can be recorded and process in that position.

In an embodiment of the present invention, the set of cabinets in the seating device holds the plurality of medical instruments, wherein the plurality of medical instruments include at least one of a device for cholesterol, a device for hemoglobin, a device for glyco-hemoglobin, a device for urine measurements, a device for gluco-meter, a device for digital stethoscope, a device for arm strength hand-grip, a USB extender from main body, a PA universal stylus pen for all touch screen for handling display, a device for spiro meter, a sound output device such as a headphone, additional ECG chest probes, or a sphygmomanometer cuff.

According to an embodiment, \ the weighing machine is attached to bottom of the body, and wherein the weighing machine is either digital or analogous.

BRIEF DESCRIPTION OF DRAWINGS

FIG. 4(*a*) illustrates rear view of the seating device as shown in FIG. 4

FIG. 4(*b*) illustrates top view of the seating device as shown in FIG. 4.

FIG. 4(*c*) illustrates right side view of the seating device as shown in FIG. 4.

FIG. 4(*d*) illustrates left side view of the seating device as shown in FIG. 4.

DETAILED DESCRIPTION

This patent describes the subject matter for patenting with specificity to meet statutory requirements. However, the description itself is not intended to limit the scope of this patent. The principles described herein may be embodied in many different forms.

Illustrative embodiments of the invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

The present invention discloses a system and a method for monitoring and recording health parameters related and not limited to non-communicable diseases or life style related disorders of a subject via a medical device in real time, and sharing the recorded health related data on a server, either a local or cloud based, for active sharing of the data with multiple remote users simultaneously anytime anywhere.

The subject as set out in the present invention is a mammal, such as a human. The subject can also include human patients.

In an embodiment, a medical device may be equipped with integrated components for recording/acquiring necessary set of data aiming at identifying the lifestyle associated non communicable diseases. It is an integrated system, which may record the following medical data parameters from individuals through interactive session of approximately 10 minutes as a package in electronically transportable form. This unique combination of parameters may be required by the corpus of specialty doctors for comprehensive health screening and analysis for early detection of the abnormal changes of the following systems, which are chronic in its development and progression due to lifestyle related complications.

Figure 1:
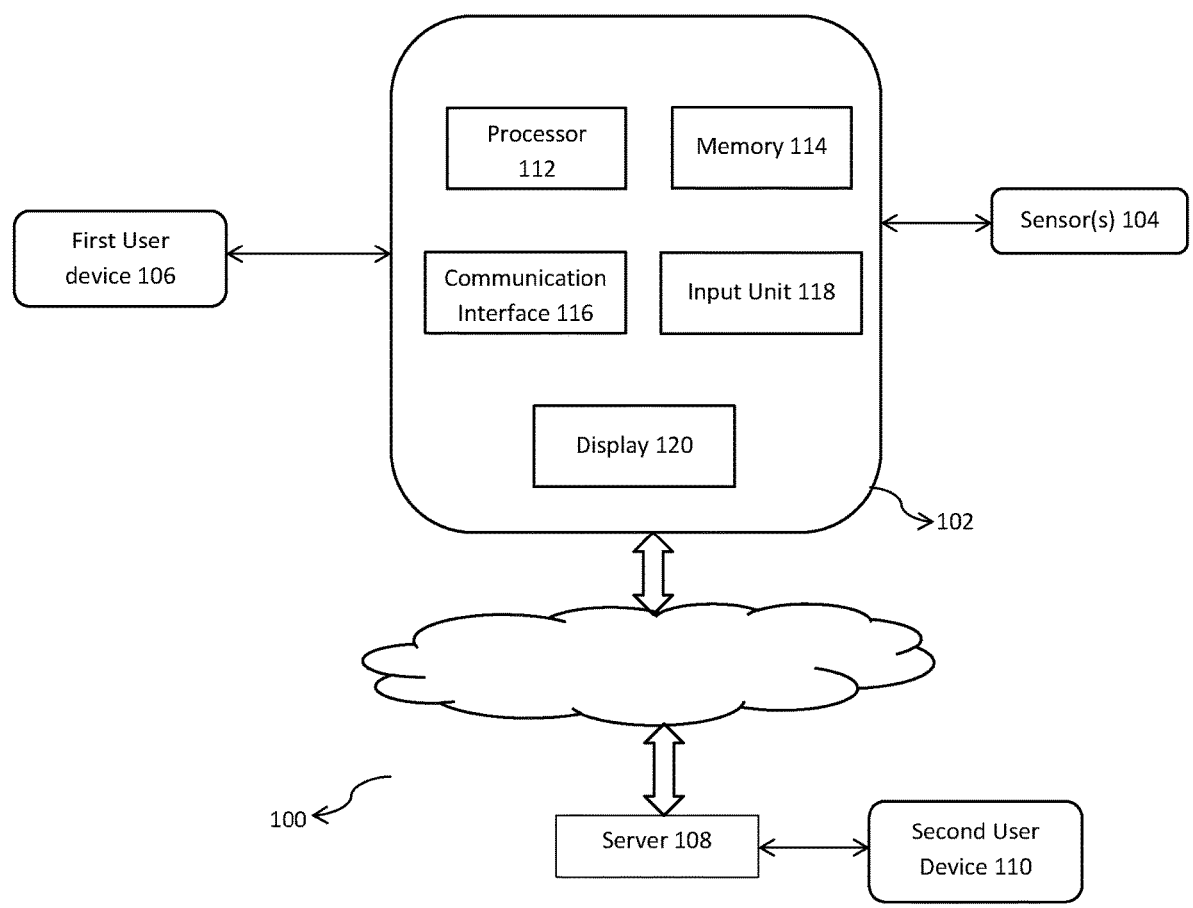
FIG. 1 illustrates an exemplary environment for a system for monitoring, recording and sharing health related including non-communicable disease related data of a subject, in accordance with an embodiment of the present invention.

Anthropometric and vital parameters: Weight, Height, BMI, Temperature, and the like Cardiovascular: Systolic Blood Pressure, Diastolic Blood Pressure, Heart-sound, ECG 6-lead and 12 lead, Pulse rate, Cardiac Auscultatory Sounds (4 areas), and the like Pulmonary function: Spirometry (PFT), SpO2, Lung Auscultatory Sounds (20 areas), and the like Geriatric (old-age) associated impairment: Cognitive function—abstract thinking, Memory function—immediate recall, Dementia, Hand-grip strength, and the like Visual impairment parameters: Colour vision, Visual acuity, and the like Auditory function: Pure tone audiometry, and the like Metabolic parameters—blood: Random Blood Sugar, HbA1c, Total Cholesterol, LDL, HDL, Triglycerides, and the like Hematologic: Hemoglobin with hematocrit, and the like Metabolic parameters—urine: Urine Glucose, Urine Protein, Urine ketone, Urine RBC, Urine Leucocytes, Urine nitrates, Urine urobilinogen, Urine Albumin Creatinine ratio, and the like FIG. 1 illustrates a system for monitoring, recording and sharing health related data of a subject, in accordance with an embodiment of the present invention. The system 100 comprises a health data capturing device 102 for recording health related data of an individual under test. The device 102 is equipped with one or more sensors 104 for sensing bio-signals from subject's body. It may be apparent to a person ordinary skilled in the art that the sensors 104 may be operably connected to the data capturing device 102 at any location with respect to the data capturing device 102, and is not restricted to one particular position or location, for e.g. the sensors may be installed at or within (or both) the data capturing device 102, or be located at a distance from the data capturing device 102, without deviating from the meaning or scope of the present invention. Further, it may also be apparent to a person ordinary skilled in the art that the data capturing device 102 may be constructed of any suitable material, such as metal, wood, plastic, and the like, without deviating from the meaning or scope of the present invention.

The system 100 further comprises a first user device 106 for viewing results of the tests or diagnoses, viewing the health-related data as and when recorded/monitored and anytime later, and if required printing or sharing those data. The system 100 further comprises a server 108 at which all the recorded data can be stored and shared. The server 108 may be either a local or a cloud based server. One or more additional units 110 which are the remote devices may access the server 108 to readily access the data stored at the server, anytime from anywhere.

The data capturing device 102 captures the health-related data of the subject. An individual under test (IUT) or the subject, during the metadata and bio-signal data capture session, is interfaced with different sensors 104, via the device 102. The IUT may be assisted by an operator, who oversees proper placement of bio-sensors, flow of operation, and insertion of meta-data and responses.

The sensors 104 receive commands for operation from the data capturing device 102. The data capturing device 102 may be embodied as any equipment or device installed or in operable communication with suitable sensors for collecting health related data for a subject, in various physical forms such a chair, a bed, a sofa, a recliner, a treadmill, a cycle, and the like without any limitation. Thus, the data capturing device 102 may also be amenable to the patient in the supine position (like bed/stretcher) and/or moving position (say treadmill). The device 102 include one or more processing units 112, memory, 114, such as primary and secondary storage, communication interfaces 116 (wired or wireless or both), such as networking/communication device endpoints, and supporting circuitry and power supply. The device 102 further includes an input unit 118 and an output unit 120. The input unit may include and is not limited to touch screen panel, non-touch screen panel, buttons or push keys, microphone, and the like. The output unit 120 may include and is not limited to a display, speaker, LEDs, LCDs, glow lights and the like. The output unit 120 serves the double purpose of displaying of the tests results, and interaction with the IUT.

The sensors 104 can be operated using the input and output units 118 and 120. The commands to operate the sensors 104 can be inputted using the input unit 118. The feedback from the sensors can be fed back to the device 102, which can be stored in the memory 114. The sensors 104 may either be directly equipped with the device 102, or they may be communicating with the device 102 via wired or wireless communication. In case of wired communication, the sensors 104 may communicate via a wired communication interface such as electric wires or cables. In case of wireless communication, the sensors 104 may communicate via a wireless communication interface such as short-range communication interface, such as Bluetooth, infrared and the like.

The recorded health data is stored in the memory 114 and can further be communicated to the first user device 106 via the communication interface 116. The first user device 106 may include and is not limited to a computer, a laptop, a smart phone, a mobile phone, a mobile device and the like. And, the first user may be a doctor in the vicinity of the IUT or the operator or a nurse etc. The data recorded may be monitored in real time on the first user device 106 using its output unit, including and not limited to display 120. Additionally, the first user may also transmit the data remotely to other users, or may also locally print the data using the first user device 106.

Further, once the bio-medical data is collected for a particular IUT, it can be transferred over cloud to a scalable server, for the remote users, such as specialty doctor to search, view, evaluate, interpret, write comments/suggestions and print reports. The scalable server 108 may be a local server or a cloud-based server. The data is shared via the server 108 with one or more second user devices 110, which are the remote users.

Figure 2:
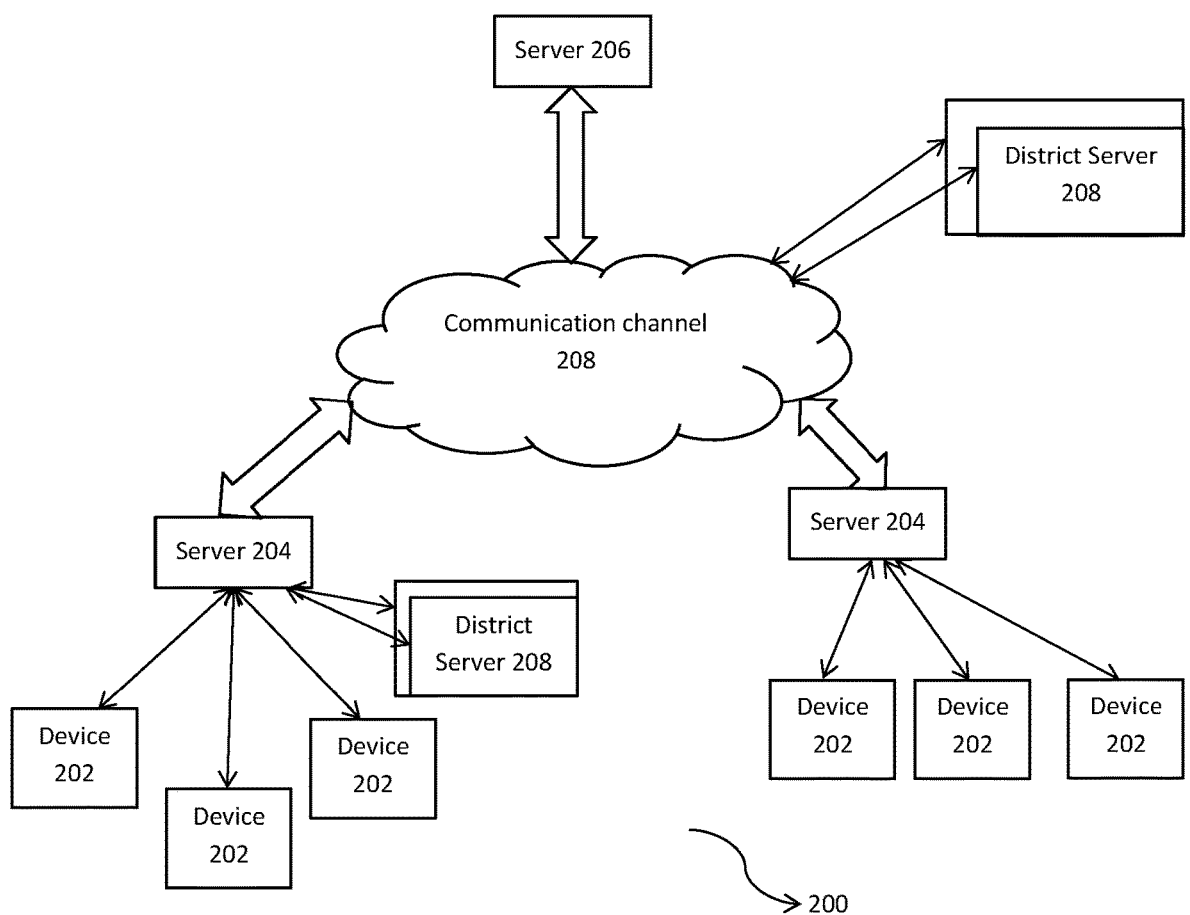
FIG. 2 illustrates an exemplary environment of a server system of monitoring, recording and sharing health related, in accordance with an embodiment of the present invention.

FIG. 2 illustrates an exemplary environment of a server system sharing data with one or more servers, where the servers further share data with one or more local servers and one or more health data capturing devices, showing seamless hierarchical system, in accordance with an embodiment of the present invention. The system generally includes the following components:

(1) Integrated Medical device (abbreviated as "IMD"): Integrated Bio-sensors in an embedded system environment to create composite data acquisition/Storge system for medical parameters. Data Capture module consisting of Inter-operability of different sensors and Internal DS.

(2) A Server, for control and management of data capture process. There may be a local storage database with the following features: redundancy; Faster data access for local IUTs; and store and forward data update option for non-continuous internet connectivity
(3) IMD Live Display: which may include with limitations an intuitive display, touch screen—no writing required, other than registration, all tests are language independent
(4) Doctor's device Display Panel: a doctor or a medical attendant may employ his connected user device to search patient by name, partial name, age range, sex, type of tests, visit dates, and any combination of these; view full patient history, all follow-up visits; evaluate health parameters; may be provided with full printable medical report generation.
(5) Cloud Server: for synchronization process.
(6) Specialty Doctor's device Display Panel It may be apparent to a person ordinary skilled in the art that the system may or may not include the above components, or may include more components without limitation, and without departing from the meaning and scope of the present invention.

In an embodiment, the system 200 shows local and cloud-based servers sharing data. The re-use of same software component as local and/or cloud level servers gives extreme flexibility in creating a deep hierarchical network of servers. The configuration of the cloud-based servers always contains the network address and credentials to connect to a parent server, if it is there.

At an exemplary situation, such as a hospital facility, let the health data capturing devices 102 may be a chair 202. Therefore, a number of chairs 202 can be connected through a LAN to a local server 204 (an instance of cloud server, deployed locally). The server aggregates health data from all the chairs 202 in the hospital and store the data locally. It does not need any internet connectivity, as all the components are connected over LAN.

Similarly, a number of such servers from different medical establishments or different locations can connect to a centrally located cloud-hosted server 206 (another instance of cloud server, deployed on cloud). This cloud-based server 206 then can aggregate data from all hospital servers centrally. The local server 204 and the cloud-based server 206 can communicate over a communication channel 208, which may be wired or wireless or both, such as including and not limiting to Ethernet, WiFi, WLAN and the like.

In another embodiment, the re-use of same component facilitates introduction of another layer in the hierarchy seamlessly. For example, the hospital servers 204 may be configured to connect to a district level server 208, and then the district level server 208 connects to the central cloud server 206. On the other hand, if the system administrator decides to remove the district servers 208 for some specific district, he can change the parent server ID of all the individual hospital servers 204, which are reporting to the specific district server 208, to the cloud server's 206 network ID.

This flexibility and on-demand hierarchy alteration is possible due to (a) Servers configuration only includes the parent server address, if any; (b) The server components in each level of hierarchy are all identical instances of cloud servers 206; and (c) Multi-system unique identifier (MSUID) mechanism, used for identification of the subject.

In an embodiment, in the Multi-system unique identifier (MSUID) mechanism, the IUTs or the register containing the details of the subject themselves and the system 100, 200 provides them with a unique identification which is uniquely associated with the IUT along with all the tests and diagnosis related to the IUT. The IUTs are identified with their unique identification all over the number of cloud servers, and hence, remotely to all the remote devices and facilities. The IUTs register themselves at the lowest level (i.e. the data capturing device 102) of the network setup. However, the captured health data from different locations is aggregated in hierarchy of servers. The system allows a. Referrals: an IUT may be referred or transferred to another hospital/super specialty facility; or any other medical establishment or health like that of a gym or any health outlet.

b. Independence of location: The IUT may present himself/herself in any of the data capturing devices 102 in the same hospital or a different hospital.

In both the cases above, the system 100, 200 ensures that the IUT is uniquely identified across hierarchy. Each IUT, during registration uses one of the Government/authorized authority issued identification document bearing an identifier, for example (in India) Aadhar card, Passport, voter ID card, PAN card, Driving license, etc. Further, the system 100, 200 encodes the type and identifier in a combined field to form a Multi-system unique identifier (MSUID). The MSUID is mapped to a local unique identifier, which encodes the identifier of the data capturing devices 102 ID.

In an embodiment, in a parent cloud server-based instance, this (MSUID, local data capturing devices 102 ID) tuple is converted to a globally unique identifier (UID) for IUT. The UID is internally maintained and mapped to all data and interactions pertaining to the IUT. Only the central server 206, which does not have any parent (i.e. the central server 206 in cloud) can have all data aggregated. All other servers in the hierarchy fetch data on-demand. The synchronization process between the components in the hierarchy ensures the matching of MSUID (without the local device identified) to ensure unique identification of each IUT. Hence, in an exemplary working embodiment, medical test involves different methods like sensing bio-signals (ECG, NIBP, Temperature, Auscultatory heart and lung sounds, SpO2, measuring respiratory volumes etc.), collecting bio-samples (blood and Urine samples), as well as interactive responses from IUT (Vision testing audiometry, Muscle strength, cognitive tests, etc.) The results of the medical tests are shown immediately as real time local display to the IUT as visual feedback, and also to an operator for correct sequencing of operations. The collected data is visible in a composite printable form to IUT as well as any doctor (locally available within the same premises—local doctor—LDOC), with a doctor's device display panel (102), and connected in the local LAN. The data may be then packetized, encrypted and stored in local database with index. The collected data is synchronized with the central database (available on cloud) through a proprietary hand-shaking command-response method. All communications are encrypted, such that data on the move are secure. An IUT can use any of his IMD in the network. Patient data transportability is achieved through the multi-system unique identifier mechanism (MSUID), explained later. Specialty doctors (SDOC) from geographically dispersed location can access individual's data through proper authentication mechanism (unique username, password and OTP). All accesses are logged, which is notifiable to the concerned individuals. Each IUT can also view his/her own data from web interface, through proper authentication mechanism (unique username, password and OTP). Each IUT is registered to the system, where unique identifier code for the user is created. The unique identifier code is synchronized with globally unique identifier through synchronization process, with the central server in cloud.

Figure 3:
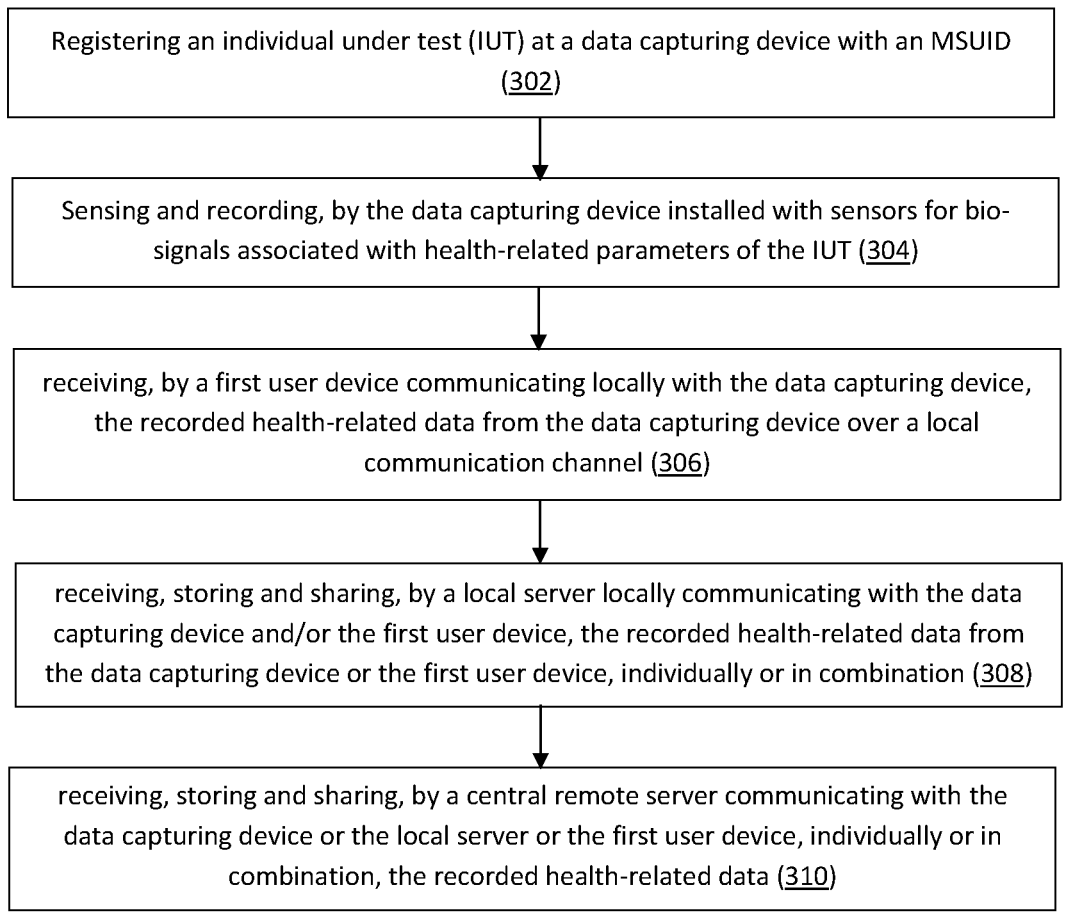
FIG. 3 illustrates an exemplary environment showing a flowchart of a method of monitoring, recording and sharing health related, in accordance with an embodiment of the present invention.

FIG. 3 illustrates an exemplary environment showing a flowchart of a method of monitoring, recording and sharing health related, in accordance with an embodiment of the present invention. The method 300 should be read and understood in conjunction with the FIGS. 1-2, and include at least one or more of the embodiments of the system described in the FIGS. 1-2. Further, the method 300 may or may not follow a step flow as described by steps 302-310 in the flowchart 300 in FIG. 3.

At a step 302, an individual under test (IUT) may be registering at a lowest level of the hierarchy of the system 200, such as at the data capturing device 102. The registration may be done by creating and using the MSUID associated with the IUT. MSUID is explained in details above in FIG. 2. Further, at step 304, health-related parameters of the IUT may be sensed and recorded, by the data capturing device 102 which is installed with sensors 104 for biosignals associated with health-related parameters of the IUT, thus identifying the lifestyle associated any disease in question. At a step 306, the recorded health-related data may be received, by the first user device 106 from the data capturing device 102, which is communicating locally with the data capturing device 102 via the communication interface 116 over a local communication channel and over the local communication channel. Thus, a first user may be informed in real time with the recorded health-related data at the first user device 106 via an output unit of the first user device 106, such as including and is not limited to a display, speaker, LEDs, LCDs, glow lights individually or in any combination. In an embodiment, the local communication channel includes and is not limited to LAN communication channel or Bluetooth or infrared, individually or in any combination.

At a step 308, the recorded health-related data may be further received, stored and shared, by a local server 204 from the data capturing device 102 or the first user device 106, the local server 204 may be locally communicating with the data capturing device 102 or the first user device 106, individually or in combination, and where the sharing is based on appropriate authentication mechanism to access the local server 204. At a step 310, the recorded health-related data may be further received, stored and shared, by a central remote server 206 from the data capturing device 102 or the local server 204 or the first user device 106, individually or in any combination, the central server 206 may be communicating with the data capturing device 102 or the local server 204 or the first user device 106, individually or in any combination, and where the sharing is based on appropriate authentication mechanism to access the central remote server 206.

In an embodiment, the configuration of the local server 204 (and any other servers such as district servers 208) includes only a parent server address associated at least with the central remote server 206 and the server components of the local server 204 and the central remote server 206 (and any other server such as district servers 208) in each level of hierarchy are all identical instances of the central remote server 206. The IUT is identified uniquely across the hierarchy by the multi-system unique identifier mechanism (MSUID) that identifies and authenticates the IUT to use and access the data capturing device 102 or the local server 204 or the central remote server 206, or the district servers 208, individually or in combination, thereby providing the method 300 with flexibility and on-demand hierarchy alteration.

In an embodiment, the method may also include a step of receiving, by a second user device 110 communicating with the central remote server 206, the recorded health-related data from the data capturing device 102 or the first user device 106 or the local server 204, individually or in combination, and informing a second user with the recorded health-related data via the second user device 106. Thus, the second user may be informed in real time with the recorded health-related data at the second user device 110 via an output unit of the second user device 110, such as including and is not limited to a display, speaker, LEDs, LCDs, glow lights individually or in any combination. In an embodiment, the local communication channel includes and is not limited to LAN communication channel or WiFi or Bluetooth or infrared, individually or in any combination. Therefore, the second user device 110 may communicate with the data capturing device 102 and the local server 204 and the first user device 106 via the central server 206.

In an embodiment, the authentication mechanism to access the local server 204 and the central remote servers 206, and the district server 208 include one or more of a user name, a password, identification information, an ID number, a PIN, an IP address, a security key, a biometric, a fingerprint, or voice, individually or in any combination, associated with a particular user who is accessing the servers, 204, 206 and 208.

Figure 4:
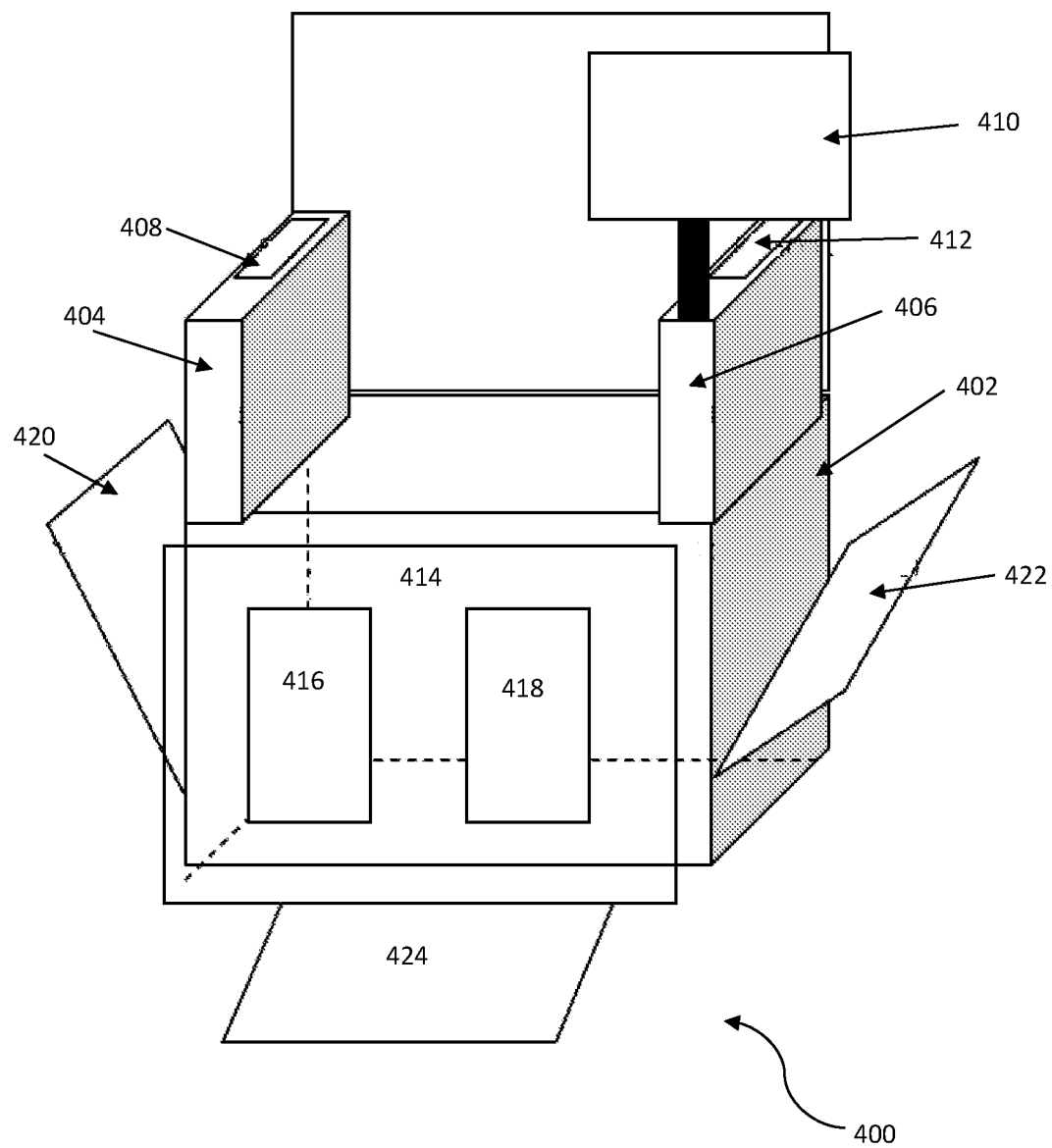
FIG. 4 illustrates a data capturing device of the system in form of a seating device, such as a chair, in accordance with an embodiment of the present device.
Figure 4:
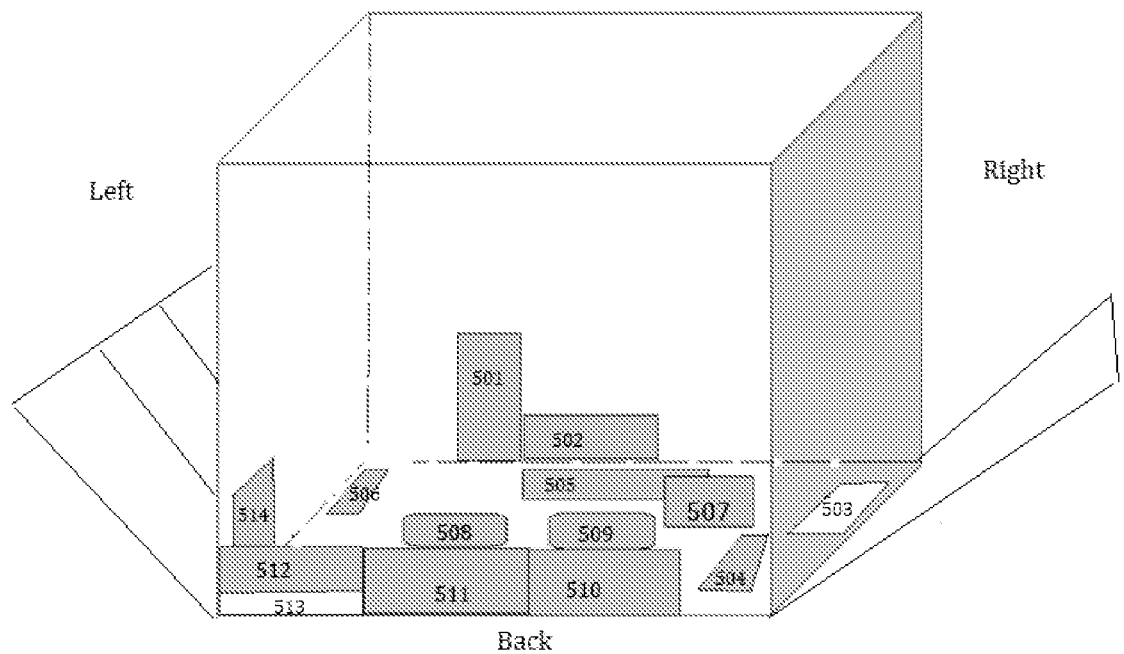
Figure 4:
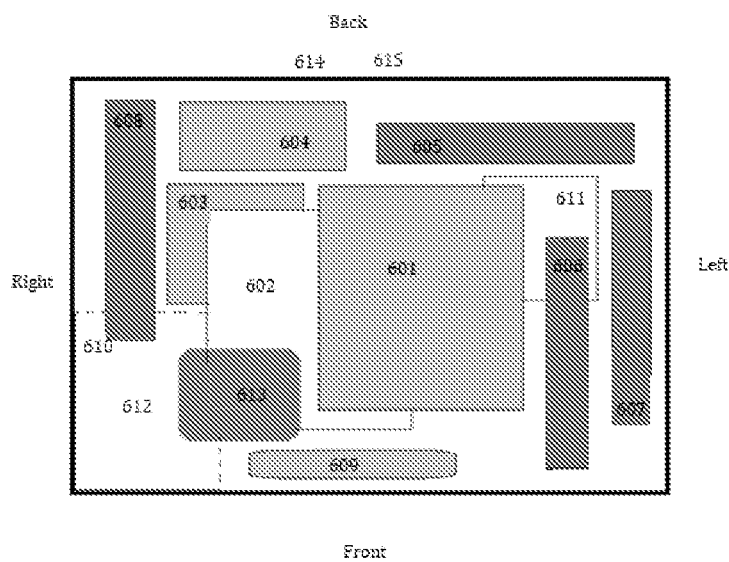
Figure 4:
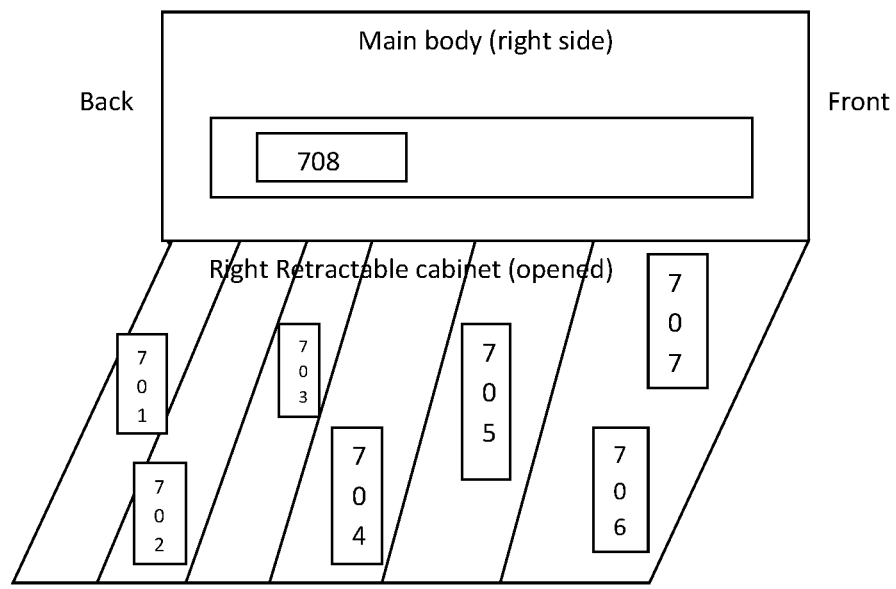
Figure 4:
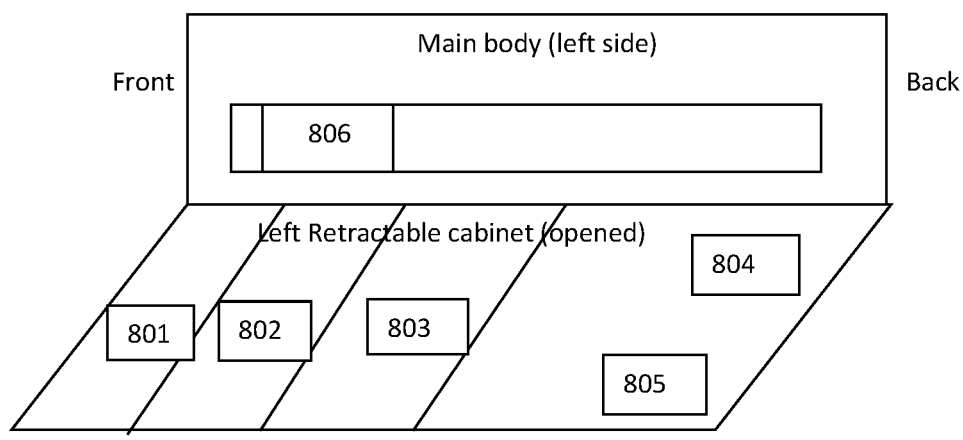

FIG. 4 illustrates the data capturing device 102 of the system 100 in form of a seating device, such as a chair, in accordance with an embodiment of the present device. FIG. 4 should be read and understood in combination with the FIGS. 1-3, and include at least one or more embodiments of the FIGS. 1-3. Also, it should be understood that the present invention is not restricted to the design, shape and operation of the device as shown in the FIG. 4, and may well include other design, shape and operation of the device that may be able to perform and fulfill the purpose of the invention, without deviating from the meaning and scope of the invention. The device can be a chair, bed, stretcher etc.

FIG. 4 shows a seating device 400, such as a chair 400, which may operate as the data capturing device 102 of the system 100. The seating device 400 may comprise of a body 402, that may further consist one or more operating components that help in operation of the seating device 400, such as including and not limited to processors, memory, drivers, installed with software components or applications for running software algorithms, power switches, power circuits, communication interfaces, display units, and other electronic/electrical/mechanical components, either individually or in any combination, and the like. For example, the seating device 400 may include a Linux Mother Board and Windows Mother Board along with their switched-mode power supply (SMPS) and hard disk drive (HDD) drive for individuals. The seating device 400 may also contain power circuits, Universal Serial Bus (USB) Extenders for communication of individual Bio Sensor interfaces. It may be apparent to a person ordinary skill in the art that the body 402 of the seating device 400 may include any number of electronic/electrical/mechanical components in any suitable configuration for its functioning without deviating from the meaning and scope of the present invention.

Further, the seating device 400 may comprise a set of arm rests 404 and 406 which are attached to the body 402 to provide arm rests to a patient sitting on the seating device 400. A right arm rest 404 may include a camera and a connection interface for operably connecting the seating device with external devices. The camera may be situated in front side to capture image/video feed of the patient, and may include and is not limited to an image camera, video camera, a web cam communicating with other devices. The connection interface may include and is not limited to a jack, such as an output Audio Jack for interfacing with audio/video devices, USB inputs and Ethernet Input Socket. Further, the right arm rest 404 may also house an Oxygen saturation finger probe and an ECG probe (408) for RA. It may be apparent to a person ordinary skill in the art that the right arm rest 404 of the seating device 400 may include any number of electronic/electrical/mechanical components and/or sensors in any suitable configuration for its functioning and/or to collect health related parameters of the patient, without deviating from the meaning and scope of the present invention.

Further, a left arm rest 406 may include an adjustable stand to hold a display unit 410 attached to the left arm rest 406. The left arm rest 406 may also house an ECG probe (412) for LA. It may be apparent to a person ordinary skill in the art that the left arm rest 406 of the seating device 400 may include any number of electronic/electrical/mechanical components and/or sensors in any suitable configuration for its functioning and/or to collect health related parameters of the patient, without deviating from the meaning and scope of the present invention.

In an embodiment, the display unit 410 may be any display or monitor for display, for example may include and is not limited to a monitor, an LED, an LCD, which may be touch screen display or non-touch for operations. In an embodiment, the display unit 410 may be attached with input unit, such as keyboard, to input data.

Furthermore, the seating device 400 may also comprise an ECG plate holder 414 attached at the bottom of the body 402 of seating device 400 around legs of the patient, which may include spring connected insulated surface to hold a set of ECG plates (416) and (418). The ECG probes 408, 412, 416 and 418 may be metal probes for right arm (RA), left arm (LA), right leg (RL) and left leg (LL) respectively. It may be apparent to a person ordinary skill in the art that the ECG probes 408, 412, 416 and 418 may act as probes for any of the right arm (RA), left arm (LA), right leg (RL) and left leg (LL) depending on the configuration and connections within the seating device 400, without deviating from the meaning and scope of the present invention.

The seating device 400 may also comprise a set of cabinets (420, 422) to hold different medical instruments. In an embodiment, the set of cabinets (420, 422) may be attached to the left and right side of the body 400, and may be retractable or foldable cabinets to hold different medical instruments on left and right side. The cabinets (420, 422) may hold instruments such as including and not limited to a device for cholesterol, a device for hemoglobin, a device for glyco-hemoglobin, a device for urine measurements, a device for gluco-meter, a device for digital stethoscope, a device for arm strength hand-grip, a USB extender from main body, a PA universal stylus pen for all touch screen for handling display, a device for spiro meter, a sound output device such as a headphone, additional ECG chest probes, sphygmomanometer cuff, and other required medical instruments. It may be apparent to a person ordinary skill in the art that set of cabinets (420, 422) may hold any number of medical instruments, without deviating from the meaning and scope of the present invention.

Also, the seating device 400 may comprise a weighing machine 424 which may be connected with the processing unit included in the body 402. The weighing machine 424 may be attached to the bottom of the body 402. In an embodiment, the weighing machine 424 may be digital or analogous.

It may be apparent to a person ordinary skilled in the art that the seating device 400 may be embodied as any device which may be installed with the sensors 104, and which a patient can use or operate in any suitable position to collect patient's health related parameters, such as the device 102 may be embodied as and not limited to a chair, a bed, a sofa, a recliner, or a cycle, and the like without any limitation.

The most preferred embodiment of the seating device with reference to its rear view (FIG. 4(*a*) illustrates rear view of the seating device as shown in FIG. 4), including locations of various components such as power extension-01 (501), power, extension-02 (502), USB Extenders-01 (503), USB Extenders-02 (504), USB Extenders-03 (505), USB Extenders-04 (506), HDD for linux (507), SMPS 01 (508), SMPS 02 (509), Linux mother board (510), Windows Mother Board (511), Main Switch Board (512), LAN switch (513) and HDD for Windows (514) have been shown in FIG. 4(*a*). Further, FIG. 4(*b*) show top view of the seating device as shown in FIG. 4 wherein the most preferred locations of various components such as Linux Mother Board (601), Windows Mother Board (602), SMPS for Linux Mother Board (603), SMPS for Windows Mother Board (604), USB Extension-01 from Linux Mother Board (605), USB Extension-02 from Linux Mother Board (606), USB Extension-03 from Linux Mother Board (607), USB Extension-04 from Windows Mother Board (608), LAN Switch (609), HDD for Windows Mother Board (610), HDD for Linux Mother Board (611), Main Power Socket (612), Multi parameter monitor (613), Power Socket (614) and Power Socket (615) have been shown. Furthermore, FIG. 4(*c*) illustrates right side view of the seating device as shown in FIG. 4 wherein the most preferred locations of various components such as device for measuring Cholesterol (701), device for measuring Hemoglobin (702), device for measuring Glyco-hemoglobin (703), device for Urine Measurements (704), Glucometer (705), digital Stethoscope (706), device for measuring Arm Strength Hand-Grip (707) and USB extender from main body(extender-07) (708) have been shown.

In addition, FIG. 4(*d*) shows left side view of the seating device as shown in FIG. 4 wherein the most preferred locations of various components such as PA universal stylus Pen for all touch screen for handling display (801), device for spiro meter (802), headphone (audio sound) (803), additional ECG chest probes (804), sphygmomanometer cuff (805), and USB extender from windows board(extender-08) (806) have been shown.

However, the invention is not restricted to the locations of the components and/or the components per se since relocations of the components and equivalent known components can be used as instead of the above-mentioned components.

It may be apparent to a person ordinary skilled in the art that the electronic/electrical/mechanical devices and the sensors, such as camera, connection interface, USB inputs and Ethernet Input Socket, ECG probes 408, 412, 416 and 418, display unit 410, and other medical instruments, may be operably connected to the seating device 400 at any location with respect to the seating device 400, and is not restricted to one particular position or location, as shown in the FIG. 4, for e.g. the sensors may be installed at or within (or both) the seating device 400, or be located at a distance from the seating device 400, without deviating from the meaning or scope of the present invention. Further, it may also be apparent to a person ordinary skilled in the art that the seating device 400 may be constructed of any suitable material, such as metal, wood, plastic, and the like, without deviating from the meaning or scope of the present invention.

Advantageously, the web-based server or the cloud-based server in the system 100 and 200 provides user interaction along with data process, display, store and generating reports all at one place, available anytime, and accessible from anywhere. The systems 100, 200 implement a web-based architecture to a data capturing embedded device (such as the device 102, 202) environment. It facilitates modularity, loose coupling and flexibility to change presentation, processing and device independence in the whole system. It has the following features:

Follows MVC (Model—view—Controller) architecture

Navigation Service: This sub-system manages test performance sequence

Internal Data store Service: a gateway and acts as a repository for all test definitions and buffers. It can be accessed by other modules through a service. During startup this module triggers all test parameters to be updated from master database. It creates and pushes commands to a command list for DataCapture module.

Database service: responsible for communicating with structured and unstructured databases Controller—service used by the user interface for communicating with the server. All are configured as web service calls.

Further, advantageously, the present invention provides the data capturing devices 102, 202 which are capable of communicating with different sensors in various communication/data exchange protocols. The communication/data exchange protocols may include and not restrict USB, Analog Audio channels, Wired Ethernet, WiFi, Bluetooth and the like.

All communication protocols are made as independent components. The communication protocols end-points are used by Input unit in Data Capturing device 102. Internal database stores the mapping between specific tests, its corresponding device (and data pattern) and the communication protocol (along with connection parameters) to be used.

As a further advantage of the present invention, all devices are implemented as separate service. Even interactive tests (e.g. vision test, audiometry, memory and cognitive tests) are modeled as separate services.

The test configurations, which include corresponding devices and data path parameters are stored in an internal database. The internal databases may include cloud-based database, or the memory 114 of the device 192. The process for monitoring and recording the health related data of an IUT starts with an Internal Data store setting up the devices, such as the devices 102, 202 with the sensors 104 and the user devices 106, for initialization, setting up command list (cmdList) and response List (data), separate for each device 102 and the user device 106. The system 100, 200 allocates Buffer in the memory 114, separate for each thread of execution, to provide insulation between tests and to avoid interference. The Controller which may be the first user device 106 or the processor 112 of the data capturing device 102 invokes of test Stop/Done command, for each of the tests selected by the user/operator. The Controller which may be the first user device 106 or the processor 112 of the data capturing device 102 communicating with each other. Any command inputted from the first user device 106 is transferred to the processor 112 of the data capturing device 102 for further processing of the commands In an embodiment, the operator may use input unit 118 of the data capturing device 102 for inputting commands and operating the device 102 along with the sensors for running the tests. In another embodiment, the operator may use the first user device 106, such as the laptop, or inputting commands and operating the device 102 along with the sensors for running the tests. In such situation, the first user device 106 is installed and downloaded with an application with a user interface, where the operator may operate the application via the user interface to give commands. The application in turn operates the sensors 104 equipped with data capturing device 102.

These commands get queued into CmdList. Data Capture device 102 or module (running as a separate process) picks up the commands from cmd List and routes to the corresponding device or sensors instance (running as different services) for acting. The device action includes starting of the test, collection of results (data) and stopping the corresponding device. Implementation as separate service makes the devices independent of each other.

When Data Capture module or the data capturing device 102 sends data to the first user device 106, or to an application running on the first user device 106, it invokes a Data Parser to parse the Raw Data recorded. The interpretation of data pattern is defined in each test definition, as separate service class implementation. A Data Sync subsystem performs data synchronization between the application running on the first user device 106 and the Data Capture module or the device 102. It runs two threads for (i) uploading device data to the application running on the first user device 106 (ii) get command list from the application running on the first user device 106. The application module calls specific Application program interface (API) to get the data for further processing and display at the first user device 106.

Further, the system 100, 200 also implements for data storage as both structured and unstructured data. The results from the tests running by the data capturing device 102 consist of both structured and unstructured databases. For example, in an embodiment, the system uses both RDMS for structured data, and noSQL database for un-structured data. Separate interfaces are provided for reading, writing and searching in the two types of databases.

In an embodiment, Structured data includes: Time stamped ECG waveform, Pulse oximeter waveform, Audiometry test values, Blood pressure results, Single values for Height, weight, temperature, SpO2, etc., values for tests related to metabolic function of individuals (Blood: Glucose, Hb, HbA1c etc., Urine: Sp.Gravity, microalbumin, WBCs, creatinine etc.)

The types of data are configured in an internal database.

In an embodiment, unstructured data includes images (scans and other penetrating images), sound files (Auscultatory Lung sounds), and interactive responses. Additionally, unstructured data are captured in the services like including and not limiting to Question Service: used for capturing the subject's medical history and current health issues, Vision Test Service: used for capturing unstructured vision test feedback, Cognitive Test Service: Used for memory test and cognitive tests.

In yet another embodiment the present invention may utilize the device for collecting medical data in order to store, record and analyze so as arrive at a predictive, prognostic, analytical, diagnostic, and therapeutic interventions.

In another embodiment the data collected in the present invention may be utilized to provide medical advice and suggest corrective measures for a better quality of life.

In another embodiment of the seating device of present invention can be a fixed device or mobile device and the mobility can be imparted by providing wheels and it can be operated manually or by machine.

The various components of the system are interlinked to one and another and function in interdepended manner. In addition, the devices of the system can be operated selectively, if so desire.

While certain embodiments have been described, these embodiments have been presented by way of example only, and are not intended to limit the scope of the present disclosure. Indeed, the novel methods, devices, and systems described herein may be embodied in a variety of other forms. Furthermore, various omissions, substitutions, and changes in the form of the methods, devices, and systems described herein may be made without departing from the spirit of the present disclosure.

We claim:

1. A system for monitoring and sharing health-related data in real time, comprising:

a data capturing device installed with one or more sensors for sensing bio-signals associated with health-related parameters of an individual under test (IUT) and recording the sensed health-related data, where the data capturing device includes a communication interface for communication;

a local server communicating locally with the data capturing device for receiving, storing and sharing the recorded health-related data, where the sharing is based on appropriate authentication mechanism to access the local server;

a central remote server communicating with the data capturing device and the local server, individually or in combination, for receiving, storing and sharing the recorded health-related data, where the sharing is based on appropriate authentication mechanism to access the central remote server;

a first user device communicating locally with the data capturing device via the communication interface over a local communication channel, where the first user device receives the recorded health-related data from the data capturing device over the local communication channel and informs a first user with the recorded health-related data; and a second user device communicating remotely with the data capturing device via the communication interface or communicating remotely with the first user device over a remote communication channel and the remote server, individually or in combination, for receiving and informing a second user with the recorded health-related data from the data capturing device or the first user device, individually or in combination, and wherein configuration of the local server (and any other server in the system) includes only a parent server address associated at least with the central remote server; and wherein server components of the local server and the central remote server (and any other server in the system) in each level of hierarchy of the system are all identical instances of the central remote server; and wherein the IUT is identified uniquely across the system by a multi-system unique identifier mechanism that identifies and authenticates the IUT to use and access the data capturing device or the local server or the central remote server, individually or in combination, thereby providing the system with flexibility and on-demand hierarchy alteration.

2. The system as claimed in claim 1, wherein the multi-system unique identifier mechanism (MSUID) is a unique identification which is uniquely associated with the IUT along with all tests and diagnosis related to the IUT, thus the IUT is identified with their unique identifier all over the hierarchy of the system including the local and the central servers, and thus, identified remotely to all devices and facilities communicating with the local and the central servers; and wherein the multi-system unique identifier mechanism for creating unique identification for the UIT is implemented at a lowest level of the hierarchy of the system including the data capturing device; and wherein the MSUID at least includes at least in part a Government/authorised authority issued identification document bearing an identifier associated with the IUT.

3. The system as claimed in claim 2, wherein the MSUID further includes a unique identifier associated with the data capturing device along with the IUT's unique identifier, and wherein all data including the tests and the results and interactions pertaining to the IUT is mapped to his/her unique MSUID, and is synchronized between components in the hierarchy of the system to ensure matching of the MSUID with the unique identification of each IUT to all the data.

4. The system as claimed in claim 2, wherein the one or more sensors are either directly integrated with the data capturing device or are communicating with the data capturing device via wired or wireless communication, individually or in combination, and wherein the wired communication include at least in part electric wires or cables, and wherein the wireless communication include short-range communication including Bluetooth or infrared individually or in combination.

5. The system as claimed in claim 4, wherein the local communication channel includes LAN communication channel or Bluetooth or infrared, individually or in any combination; and wherein the remote communication channel includes wireless LAN, WAN, Internet, Ethernet, WiFi, WLAN, cellular communication channel, individually or in any combination, wherein the recorded health-related data is collected for a particular IUT and is transferred to a scalable server including the local and over cloud to the central remote servers, via the first user device or the second user device or the data capturing device, individually in any combination, for informing the first and the second users, including at least local attendants, operators, nurses, doctors, specialty doctor, to search, view, evaluate, interpret, write comments/suggestions and print health-related reports.

6. The system as claimed in claim 5, wherein the recorded health-related data is collected for a particular IUT and is transferred to a scalable server including the local and over cloud to the central remote servers, via the first user device or the second user device or the data capturing device, individually in any combination, for informing the first and the second users, including at least local attendants, operators, nurses, doctors, specialty doctor, to search, view, evaluate, interpret, write comments/suggestions and print health-related reports.

7. The system as claimed in claim 2, wherein the data capturing device further include one or more processing units, memory storage, supporting circuitry and power supply, and wherein the communication interface is a wired or wireless interface, individually or in combination; and the data capturing device further includes an input unit and an output unit, and wherein the one or more sensors are operated using the input and output units; and wherein the input unit includes touch screen panel, non-touch screen panel, buttons or push keys, microphone, individually or in any combination; and wherein the output unit includes a display, speaker, LEDs, LCDs, glow lights individually or in any combination, and wherein the output unit serves a double purpose of displaying of the tests results, and interaction with the IUT.

8. The system as claimed in claim 7, wherein the first user device and the second user device include a computer, a laptop, a smart phone, a mobile phone, a mobile device individually or in any combination; and wherein the health-related data recorded is monitored in real time on the first user device and the second user device using an output unit, including at least a display; and wherein the first user device and the second user device print the health-related data at a printer.

9. The system as claimed in claim 6, wherein the system further includes one or more district servers communicating with the local server which in turn communicates with the central remote server, in the hierarchy of the system, and wherein the any other server in the system includes at least the district servers, and wherein the configuration of the district server includes only a parent server address associated at least with the central remote server; and wherein server components of the local server, the district servers and the central remote server in each level of hierarchy of the system are all identical instances of the central remote server, thereby providing the system with flexibility and on-demand hierarchy alteration, and wherein the one or more district servers are removable from the hierarchy of the system, by simply changing the parent server ID of all individual local servers, which are reporting to the specific district server, to the central remote server's network ID, and wherein the authentication mechanism to access the local and the central remote servers include one or more of a user name, a password, identification information, an ID number, a PIN, an IP address, a security key, a biometric, a fingerprint, or voice, individually or in any combination.

10. A method for monitoring and sharing health-related data in real time, comprising:
    sensing, by a data capturing device installed with one or more sensors for bio-signals associated with health-related parameters of an individual under test (IUT);
    recording, by the data capturing device, the sensed health-related data, where the data capturing device includes a communication interface for communication;
    receiving, by a first user device communicating locally with the data capturing device via the communication interface over a local communication channel, the recorded health-related data from the data capturing device over the local communication channel and informing a first user with the recorded health-related data via the first user device;
    receiving, storing and sharing, by a local server locally communicating with the data capturing device or the first user device, the recorded health-related data from the data capturing device or the first user device, individually or in combination, where the sharing is based on appropriate authentication mechanism to access the local server; and
    receiving, storing and sharing, by a central remote server communicating with the data capturing device or the local server or the first user device, individually or in any combination, the recorded health-related data from the data capturing device or the local server or the first user device, individually or in any combination, where the sharing is based on appropriate authentication mechanism to access the central remote server; and
    receiving, by a second user device communicating with the central remote server, the recorded health-related data from the data capturing device or the first user device or the local server, individually or in combination, and informing a second user with the recorded health-related data via the second user device, and
    wherein configuration of the local server (and any other server in the method) includes only a parent server address associated at least with the central remote server; and wherein server components of the local server and the central remote server (and any other server in the method) in each level of hierarchy are all identical instances of the central remote server; and wherein the IUT is identified uniquely across the hierarchy by a multi-system unique identifier mechanism that identifies and authenticates the IUT to use and access the data capturing device or the local server or the central remote server, individually or in combination, thereby providing the method with flexibility and on-demand hierarchy alteration.

11. The method as claimed in claim 10, wherein the IUT is uniquely identified by the multi-system unique identifier mechanism (MSUID) which is uniquely associated with the IUT along with all tests and diagnosis related to the IUT, thus the IUT is identified with their unique identifier all over the hierarchy including the local and the central servers, and thus, identified remotely to all devices and facilities communicating with the local and the central servers; and wherein the multi-system unique identifier mechanism for creating unique identification for the UIT is implemented at a lowest level of the hierarchy including the data capturing device; and wherein the MSUID at least includes at least in part a Government issued identification document bearing an identifier associated with the IUT.

12. The method as claimed in claim 11, wherein the one or more sensors are either directly integrated with the data capturing device or are communicating with the data capturing device via wired or wireless communication, individually or in combination, and wherein the one or more sensors communicate with the data capturing device via wired communication or wireless communication, individually or in combination, wherein the wired communication including at least in part electric wires or cables, and wherein the wireless communication include short-range communication including Bluetooth or infrared individually or in combination; and wherein the one or more sensors communicate with the data capturing device via wired communication or wireless communication, individually or in combination, wherein the wired communication including at least in part electric wires or cables, and wherein the wireless communication include short-range communication including Bluetooth or infrared individually or in combination.

13. The method as claimed in claim 12, wherein the local communication channel includes LAN communication channel or Bluetooth or infrared, individually or in any combination; and wherein the remote communication channel includes wireless LAN, WAN, Internet, Ethernet, WiFi, WLAN, cellular communication channel, individually or in any combination.

14. The method as claimed in claim 13, wherein the method further includes one or more district servers communicating with the local server which in turn communicates with the central remote server, in hierarchy, and wherein the any other server in the method includes at least the district servers, and wherein the configuration of the district server includes only a parent server address associated at least with the central remote server; and wherein server components of the local server, the district servers and the central remote server in each level of hierarchy are all identical instances of the central remote server, thereby providing the method with flexibility and on-demand hierarchy alteration.

15. The method as claimed in claim 12, where in the one or more district servers are removable from the hierarchy, by simply changing the parent server ID of all individual local servers, which are reporting to the specific district server, to the central remote server's network ID.

16. A seating device for monitoring and sharing health-related data of an individual under test (IUT) in real time, comprising
- a body including one or more operating electronic/electrical/mechanical/software components, either individually or in any combination, for controlling operation of the seating device;
- a set of arm rests attached to the body to provide arm rests to the individual under test (IUT), the set of arm rests including and supporting a camera to capture image/video feed of the individual under test (IUT), a communication interface for operably connecting the seating device with external devices, an Oxygen saturation finger probe, a set of ECG probes for right and left arms of the individual under test (IUT) and an adjustable stand to hold a display unit for display;
- an ECG plate holder, attached at the bottom of the body, including a spring connected insulated surface to hold a set of ECG plates for right leg and left leg;
- a set of retractable cabinets, attached to left and right side of the body, to hold a plurality of medical instruments; and
- a weighing machine communicating with the operating electronic/electrical/mechanical/software components of the body, either individually or in any combination, and where the weighing machine is operably attached to the body.

17. The seating device as claimed in claim 16, wherein the operating electronic/electrical/mechanical/software components of the body include one or more of processors, memory, drivers, installed with software components or applications for running software algorithms, power switches, power circuits, communication interfaces, or display units, either individually or in any combination, and wherein the seating device includes a Linux Mother Board and Windows Mother Board along with their SMPS and HDD drive for individuals, power circuits, USB Extenders for communication of individual Bio Sensor interfaces; and wherein the camera is situated in front side to capture image/video feed of the individual under test (IUT), and the camera is an image camera, or a video camera, or a web cam, either individually or in any combination, communicating with external devices, and wherein the communication interface includes at least one of a jack, an output Audio Jack for interfacing with audio/video devices, USB inputs and an Ethernet Input Socket, either individually or in any combination; and wherein the display unit is a display or a monitor for display, and wherein the display unit includes a monitor, an LED, or an LCD, and the display unit is either a touch screen display or a non-touch screen display for operations; and wherein the display unit is attached with input unit including a keyboard, to input data.

18. The seating device as claimed in claim 17, wherein the set of cabinets holds the plurality of medical instruments, wherein the plurality of medical instruments include at least one of a device for measuring cholesterol, a device for measuring hemoglobin, a device for measuring glyco-hemoglobin, a device for urine measurements, gluco-meter, digital stethoscope, a device for measuring arm strength hand-grip, a USB extender from main body, a PA universal stylus pen for all touch screen for handling display, a device for spiro meter, a sound output device such as a headphone, additional ECG chest probes, or a sphygmomanometer cuff, and wherein the weighing machine is attached to bottom of the body; and wherein the weighing machine is either digital or analogous.

19. The seating device as claimed in claim 16, wherein the device is a fixed device or mobile device, and the mobility can be imparted by providing wheels/rollers and it can be operated manually or by machine, and wherein the device can be chair, a bed, a sofa, a recliner, a treadmill, a cycle, stretcher, and the like and these device can be made of any suitable materials such as metal, wood, plastic, and the like; and wherein the leg rest, backrest and armrest can be selectively folded in order to change the shape of the structures into horizontal/supine positions so that the subject can lying down and all health parameters can be recorded and process in that position.

* * * * *